United States Patent
Helmer

(10) Patent No.: US 11,878,152 B2
(45) Date of Patent: Jan. 23, 2024

(54) DETERMINING A STATUS OF AN INJECTION

(71) Applicant: Sanofi, Paris (FR)

(72) Inventor: Michael Helmer, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/077,642

(22) Filed: Dec. 8, 2022

(65) Prior Publication Data

US 2023/0108085 A1    Apr. 6, 2023

Related U.S. Application Data

(63) Continuation of application No. 16/954,406, filed as application No. PCT/EP2018/085391 on Dec. 18, 2018, now Pat. No. 11,559,629.

(30) Foreign Application Priority Data

Dec. 21, 2017 (EP) ..................... 17306869

(51) Int. Cl.
*A61M 5/315* (2006.01)
*A61M 5/32* (2006.01)

(52) U.S. Cl.
CPC ...... *A61M 5/31553* (2013.01); *A61M 5/3159* (2013.01); *A61M 5/31546* (2013.01); *A61M 5/3202* (2013.01); *A61M 2205/50* (2013.01)

(58) Field of Classification Search
CPC .......... A61M 5/31553; A61M 5/31546; A61M 5/3159; A61M 5/3202; A61M 2205/50
See application file for complete search history.

(56) References Cited

U.S. PATENT DOCUMENTS

| 2003/0060768 | A1 | 3/2003 | Kiyatake et al. |
| 2008/0169307 | A1* | 7/2008 | Hofstetter ........... A61M 5/3155 222/14 |
| 2012/0153027 | A1 | 6/2012 | Dawber |
| 2012/0245515 | A1* | 9/2012 | Calasso ................ A61M 5/50 604/67 |

(Continued)

FOREIGN PATENT DOCUMENTS

| CN | 1406641 | 4/2003 |
| CN | 101909673 | 12/2010 |

(Continued)

OTHER PUBLICATIONS

Translation (Year: 2010).*

(Continued)

*Primary Examiner* — Dung T Ulsh
(74) *Attorney, Agent, or Firm* — Fish & Richardson P.C.

(57) ABSTRACT

An electronic device comprising: a housing for attachment to an injection device; a first sensor assembly comprising a first coil and two magnets of opposite polarity, wherein the first coil is configured to provide a first voltage pulse as a first Wiegand wire of the injection device moves from a first position proximate to one of the magnets of the first sensor assembly to a second position proximate to the other magnet of the first sensor assembly; and one or more processors configured to enter an enabled state from a sleep state after receiving the first voltage pulse from the first coil.

20 Claims, 7 Drawing Sheets

(56) References Cited

U.S. PATENT DOCUMENTS

| | | | |
|---|---|---|---|
| 2015/0290395 A1 | 10/2015 | Jugl et al. | |
| 2015/0290396 A1* | 10/2015 | Nagar | G16H 20/13 340/540 |
| 2017/0343385 A1 | 11/2017 | Mehnert et al. | |
| 2018/0064879 A1 | 3/2018 | Sall et al. | |
| 2018/0207366 A1 | 7/2018 | Marcoz et al. | |
| 2018/0225560 A1 | 8/2018 | Schneider et al. | |

FOREIGN PATENT DOCUMENTS

| | | | |
|---|---|---|---|
| CN | 107405453 | 11/2017 | |
| DE | 102008031795 | 1/2010 | |
| DE | 102008031795 A1 * | 1/2010 | A61M 5/31525 |
| EP | 3075404 | 10/2016 | |
| JP | S47-028850 | 11/1972 | |
| JP | 2003-090702 | 3/2003 | |
| JP | 2017-524399 | 8/2017 | |
| JP | 2017-525473 | 9/2017 | |
| WO | WO 2009/083600 | 7/2009 | |
| WO | WO 2016/142216 | 9/2016 | |
| WO | WO 2017/013463 | 1/2017 | |
| WO | WO 2017/059553 | 4/2017 | |

OTHER PUBLICATIONS

Dlugos, "Wiegand Effect Sensors Theory and Applications", Sensors Magazine Online, May 1998, 4 pages.
International Preliminary Report on Patentability in International Appln. No. PCT/EP2018/085391, dated Jun. 23, 2020, 6 pages.
International Search Report and Written Opinion in International Appln. No. PCT/EP2018/085391, dated Feb. 22, 2019, 9 pages.

* cited by examiner

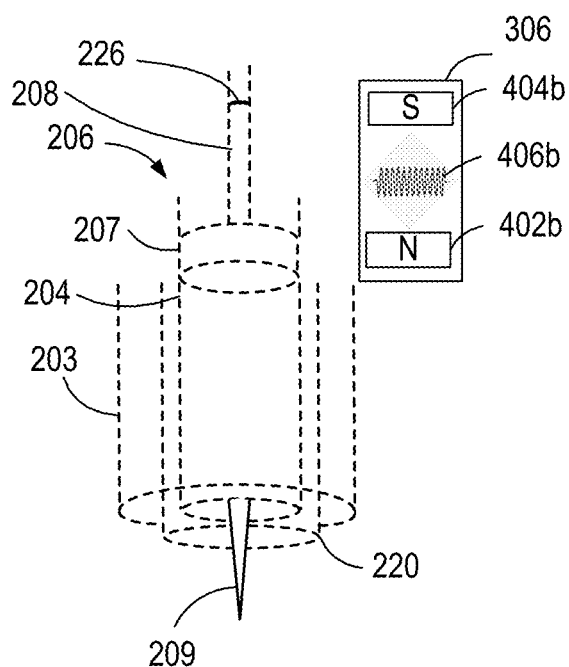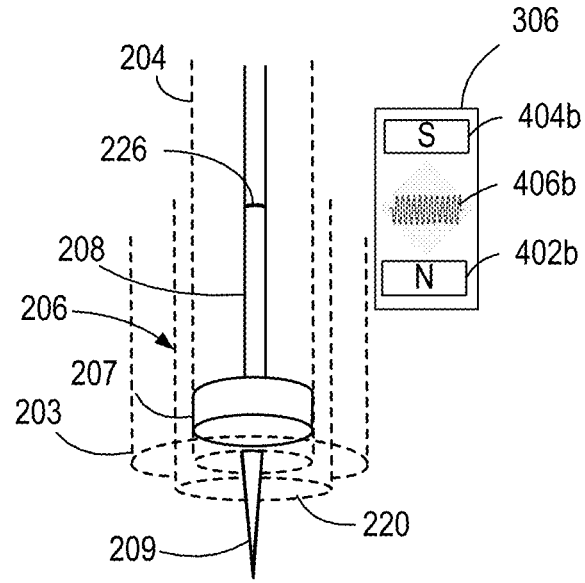
FIG. 6A
FIG. 6B
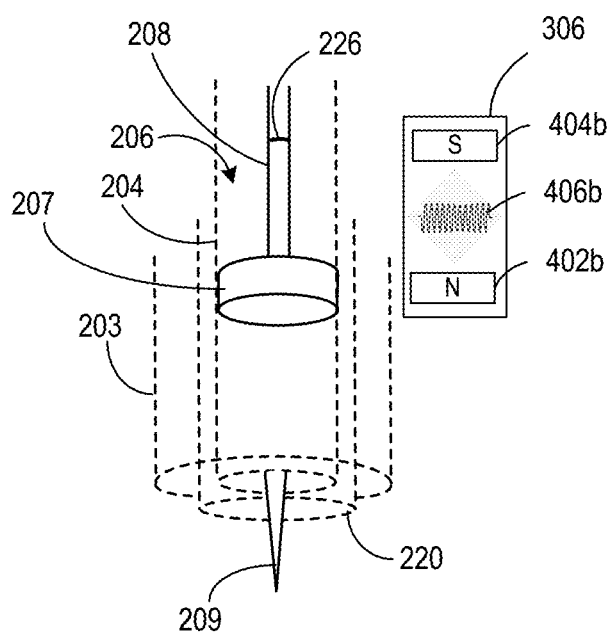
FIG. 6C

DETERMINING A STATUS OF AN INJECTION

CROSS-REFERENCE TO RELATED APPLICATIONS

This application is a continuation of U.S. application Ser. No. 16/954,406, filed Jun. 16, 2020, which is a National Stage Application under 35 U.S.C. § 371 and claims the benefit of International Application No. PCT/EP2018/085391, filed Dec. 18, 2018, which claims priority to European Application No. 17306869.3, filed Dec. 21, 2017, the disclosures of each of which are incorporated herein by reference in their entireties.

TECHNICAL FIELD

This disclosure relates to determining a status of an injection, and more particularly, to determining a status of an injection of medicament administered by an injection device.

BACKGROUND

A variety of diseases can be treated by injection of a medicament. Such injection can be performed using injection devices, which are applied either by medical personnel or by patients themselves. As an example, type-1 and type-2 diabetes can be treated by patients themselves by injection of insulin doses, for example once or several times per day. For instance, a pre-filled disposable insulin pen or autoinjector can be used as an injection device. Alternatively, a re-usable pen or autoinjector may be used. A disposable or re-usable pen or autoinjector allows replacement of an empty medicament cartridge by a new one. Either type of pen or autoinjector may come with a set of one-way needles that are replaced before each use.

SUMMARY

In an aspect, an electronic device includes a housing for attachment to an injection device and a first sensor assembly. The first sensor assembly includes first coil and two magnets of opposite polarity. The first coil is configured to provide a first voltage pulse as a first Wiegand wire of the injection device moves from a first position proximate to one of the magnets of the first sensor assembly to a second position proximate to the other magnet of the first sensor assembly. The electronic device also includes one or more processors configured to enter an enabled state from a sleep state after receiving the first voltage pulse from the first coil.

Implementations can include one or more of the following features.

In some implementations, the one or more processors consume no power when the one or more processors are in the sleep state.

In some implementations, the one or more processors are configured to process data when the one or more processors are in the enabled state.

In some implementations, the one or more processors are configured to receive the first voltage pulse from the first coil. A time of receipt of the first voltage pulse is indicative of a start time of an injection of a medicament by the injection device.

In some implementations, the electronic device includes a second sensor assembly that includes a second coil and two magnets of opposite polarity. The second coil is configured to provide a second voltage pulse as a second Wiegand wire of the injection device moves from a first position proximate to one of the magnets of the second sensor assembly to a second position toward the other magnet of the second sensor assembly. The one or more processors are configured to receive the second voltage pulse from the second coil. A time of receipt of the second voltage pulse is indicative of an end time of the injection.

In some implementations, each of the first Wiegand wire and the second Wiegand wire includes an outer shell and an inner core. A magnetic coercivity of the outer shell is larger than a magnetic coercivity of the inner core.

In some implementations, each of the first voltage pulse and the second voltage pulse has a magnitude that satisfies a predetermined threshold.

In some implementations, the first Wiegand wire is affixed to a needle shield of the injection device and the second Wiegand wire is affixed to a drive mechanism of the injection device.

In some implementations, the first sensor assembly is positioned proximate to the needle shield and the second sensor assembly is positioned proximate to the drive mechanism.

In some implementations, the first voltage pulse is provided as the needle shield moves from an extended position to a retracted position, and the second voltage pulse is provided when the drive mechanism is substantially extended.

In some implementations, one or both of the time of receipt of the first voltage pulse and the time of receipt of the second voltage pulse are stored in one or more non-transitory computer-readable medium.

In some implementations, the one or more non-transitory computer-readable medium includes a non-volatile memory that is configured for storing data absent a continuous power supply.

In some implementations, the memory is ferroelectric random access memory (FRAM).

In some implementations, the one or more processors are configured to transmit one or both of the time of receipt of the first voltage pulse and the time of receipt of the second voltage pulse to a computing device.

In some implementations, one or both of the time of receipt of the first signal and the time of receipt of the second signal are transmitted wirelessly.

In some implementations, one or both of the time of receipt of the first signal and the time of receipt of the second signal are transmitted over a Universal Serial Bus (USB) interface.

In some implementations, the housing is sleeve-shaped and is configured to removably attach around an external housing of the injection device.

In another aspect, a system includes an injection device that includes a needle shield. A Wiegand wire is affixed to the needle shield. The system also includes an electronic device for attachment to the injection device. The electronic device includes a sensor assembly that includes a coil and two magnets of opposite polarity. The coil is configured to provide a voltage pulse as the Wiegand wire moves from a first position proximate to one of the magnets to a second position proximate to the other magnet. The electronic device also includes one or more processors configured to enter an enabled state from a sleep state after receiving the voltage pulse from the coil.

In another aspect, a system includes a variable dose injection device that includes a dosage knob and a plurality of Wiegand wires positioned around a perimeter of the dosage knob. Each Wiegand wire corresponds to an increment of a dosage of a medicament to be injected by the variable dose injection device. The system also includes an electronic device configured for attachment to the variable dose injection device. The electronic device includes a sensor assembly that includes a coil and two magnets of opposite polarity. The coil is configured to provide a voltage pulse for each of the plurality of Wiegand wires that moves from a first position proximate to one of the magnets to a second position proximate to the other magnet. The electronic device also includes one or more processors configured to receive the voltage pulses and cause a counter to be incremented for each voltage pulse that is received. A value stored by the counter corresponds to the dosage of the medicament to be injected by the variable dose injection device.

In another aspect, a method includes receiving, by an electronic device configured for attachment to an injection device, a voltage pulse from a coil of a sensor assembly as a Wiegand wire of the injection device moves from a first position to a second position. The first position is proximate to one magnet corresponding to the sensor assembly and the second position is proximate to another magnet corresponding to the sensor assembly. The magnets have opposite polarities. The method also includes entering, by the electronic device, an enabled state from a sleep state after receiving the voltage pulse from the coil.

DESCRIPTION OF DRAWINGS

FIGS. 6A-C show various positions of a second Wiegand wire of the injection device relative to the second sensor assembly.

Like reference symbols in the various drawings indicate like elements.

DETAILED DESCRIPTION

Figure 1:
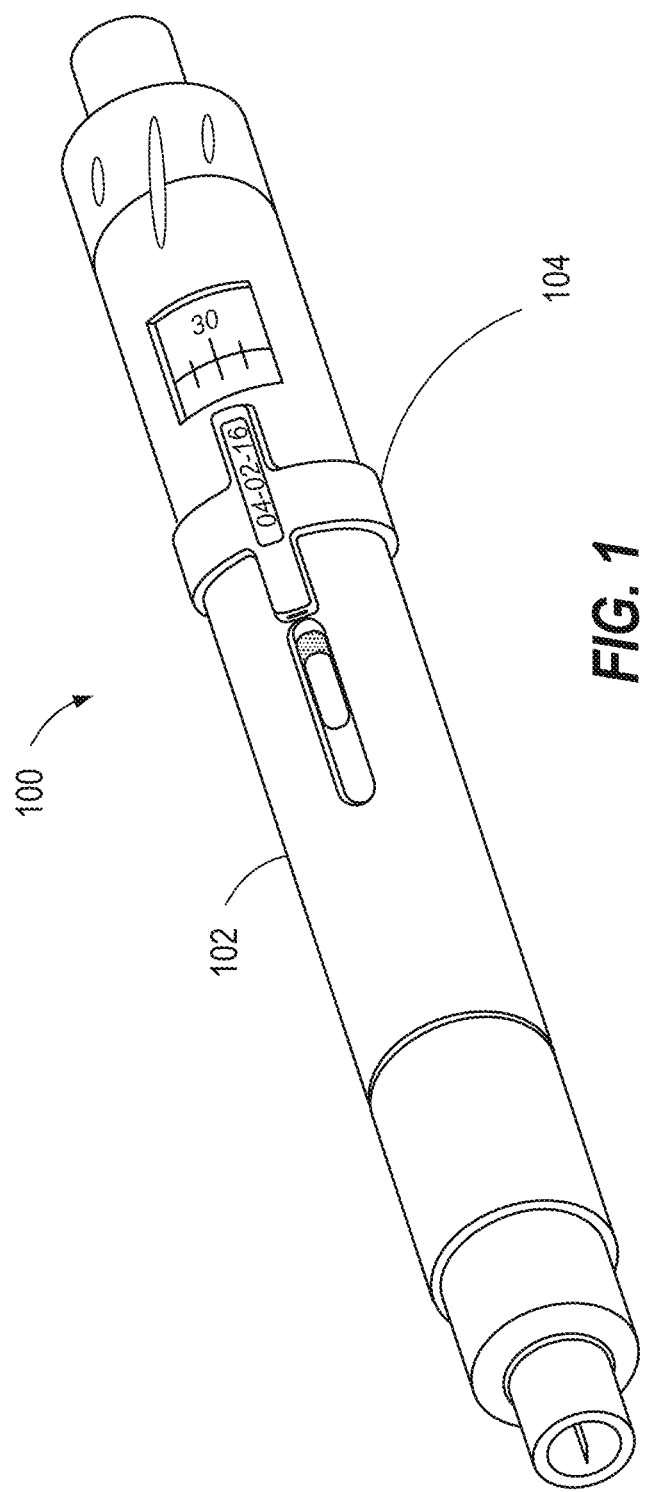
FIG. 1 is an example of a system for awaking an injection device and/or determining a status of an injection of a medicament.

Described herein is a drug delivery device that is configured to identify events related to a medicament injection, such as a start time of the injection, an end time of the injection, and a hold time of the injection, among others. The drug delivery device may include an add-on device that includes various components and electronics configured to identify such events based on interaction with Wiegand wires affixed to and/or incorporated in components of the drug delivery device. A Wiegand wire is a wire that includes an outer shell and an inner core, such that a magnetic coercivity of the outer shell is larger (e.g., significantly larger) than a magnetic coercivity of the inner core. The Wiegand wire exhibits a relatively large magnetic hysteresis that causes a voltage pulse/spike to be produced in a coil of the add-on device when a magnetic threshold is reached (e.g., when the Wiegand wire is positioned at a particular location relative to a magnet of the add-on device).

In some implementations, the voltage pulse may cause the add-on device to awaken (e.g., "wake up" from a sleep state into an enabled state). For example, the add-on device may initially be in a sleep state in which the add-on device consumes little or no power. After receipt of the voltage pulse, the add-on device may wake up such that electronics of the add-on device enter a state in which the electronics can process data and/or signals from one or more electrical components (e.g., sensors of the add-on device, separate sensors, etc.).

In some implementations, a needle shield of the drug delivery device may include a first Wiegand wire, and the add-on device may be configured to determine a position of the first Wiegand wire (and thus a position of the needle shield) at various points in time. The determined position of the needle shield at a first time can be used to determine the start time of the injection, and the determined position of the needle shield at a second time can be used to determine the hold time of the injection. Similarly, a drive mechanism of the drug delivery device may include a second Wiegand wire, and the add-on device may be configured to determine a position of the second Wiegand wire (and thus a position of the drive mechanism) at various points in time. The determined position of the drive mechanism at a third point in time can be used to determine the end time of the injection.

The subject matter described herein will largely be described with reference to a drug delivery device such as an injection device (e.g., an insulin injection device), such as a disposable or re-usable injection device. However, the systems and techniques described herein are not limited to such applications, and may equally well be deployed with injection devices that eject other medicaments, or with other types of medical devices (e.g., pumps). In other words, the systems and techniques described herein can be used to enable electronics of other devices and/or cause information related to injections by other devices to be recorded.

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

FIG. 1 is an example of a system 100 for awaking an injection device and/or determining a status of an injection of a medicament. The system 100 includes an injection device 102 and an add-on device 104 that may be removably attached to the injection device 102. The injection device 102 may be a pre-filled, disposable or reusable injection pen that is configured to hold and dispense the medicament to a patient. The add-on device 104 may be an electronic device (e.g., a computing device). The system 100 may be used, for example, to determine a status of an insulin injection administered by the injection device 102 using the add-on device 104. Status information may include a start time of the injection, an end time of the injection, a hold time of the injection, etc. Additional status information may be determined based on the start, end, and/or hold times, such as a duration of the injection, among others. Such status information may be used to record a history of one or more injections provided by the injection device 102.

In general, the injection device 102 allows for selection and dispensing of a selected dosage of a medicament to the patient. With the add-on device 104 attached to the injection device 102, a dosage of the medicament may be administered. The add-on device 104 is configured to identify various events and/or states of the injection device 102 and corresponding times at which the events/states occur based on interactions between components of the add-on device 104 and components of the injection device 102. For example, the add-on device 104 may be configured to determine the start time of the injection by identifying a time at which a needle shield (220 of FIG. 2) of the injection device 102 retracts (e.g., signifying that the injection device 102 has been or is being placed against the patient's skin); the add-on device 104 may be configured to determine the end time of the injection by identifying a time at which a drive mechanism (206 of FIG. 2) of the injection device 102 is substantially extended (e.g., signifying that the medicament has been substantially ejected); the add-on device 104 may be configured to determine the hold time of the injection by identifying a time at which the needle shield 220 of the injection device 102 extends (e.g., signifying that the injection device 102 has been or is being removed from the patient's skin).

Figure 2:
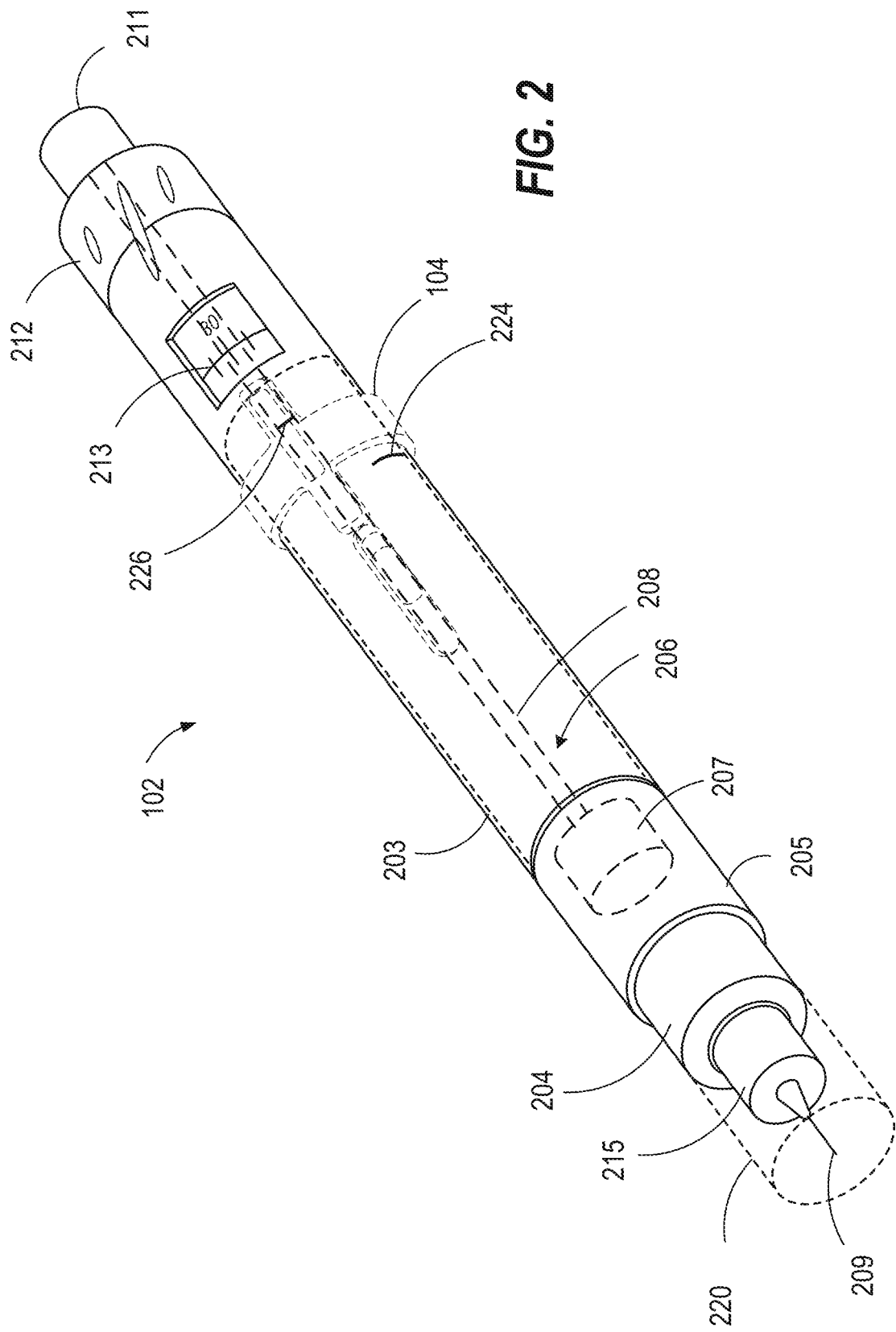
FIG. 2 is an example of the injection device of FIG. 1.

FIG. 2 is an exploded view of an example of the injection device 102 of FIG. 1. The injection device 102 may be a pre-filled, disposable or reusable injection pen. The injection device 102 includes a housing 203 and a cartridge 204. The cartridge 204 is configured to hold a volume of medicament (e.g., in fluid form). In some implementations, the cartridge 204 is a medicament container, such as an insulin container. In some implementations, a portion of the cartridge 204 may reside within the housing 203 of the injection device 102 and/or a cartridge housing 205, and therefore may not be readily visible.

The injection device 102 includes a drive mechanism 206 that is configured to cause the medicament to be ejected from the cartridge 204. The drive mechanism 206 includes a stopper 207 that is movably disposed in the cartridge 204 and a piston 208 (e.g., a plunger arm). The piston 208 is configured to cause the stopper 207 to move from a distal end of the cartridge 204 toward a proximal end of the cartridge 204, thereby causing the fluid to be dispensed through the proximal end of the cartridge 204. The injection device 102 also includes a needle assembly 215 that is disposed at the proximal end of the cartridge 204. The needle assembly 215 includes an aperture through which the fluid is dispensed. A needle 209 can be affixed to the needle assembly 215 proximate to the aperture such that the fluid travels through the aperture and the needle 209 when dispensed. In some implementations, the needle assembly 215 and/or the needle 209 are threaded such that the needle 209 can be screwed onto the needle assembly 215. In some implementations, the cartridge 204 is threaded such that the needle assembly 215 can be screwed onto the cartridge 204.

The needle 209 can be protected by a needle shield 220 that prevents inadvertent contact with the needle 209. The needle shield 220 is a tube-shaped structure that is positioned along a length of the injection device 102 within the housing 203. The needle shield 220 may be configured to move between an extended position and a retracted position. In the example illustrated in FIG. 2, the needle shield 220 is in the extended position to minimize and/or prevent inadvertent contact with the needle 209. The needle shield 220 is typically configured to remain in the extended position by default (e.g., in the absence of pressure being applied to the needle shield 220). When the injection device 102 (and, e.g., in particular, the needle shield 220) is placed against the patient's skin and pressure is applied towards the patient's skin, the needle shield 220 is configured to move from the extended position toward the retracted position, thereby causing the needle 209 to insert into the patient's skin. In some implementations, the needle shield 220 may have a telescopic configuration that allow the needle shield 220 to retract into the housing 203 of the injection device 102 when pressure is applied.

A medicament dose (e.g., such as an insulin dose) to be ejected from injection device 102 can be selected by turning a dosage knob 212, and the selected dose can be displayed by a dosage window 213. In some examples, the dosage window 213 is a display, such as an electronic display. In some examples, the selected dose can be displayed in multiples of International Units (IU), wherein one IU is the biological equivalent of about 45.5 micrograms of medicament such as pure crystalline insulin (e.g., $\frac{1}{22}$ mg). An example of a selected dose displayed in the dosage window 213 may, for example, be 30 IUs, as shown in FIG. 2. In some examples, the selected dose may be displayed differently, for example, by a non-electronic display. In some examples, the dosage window 213 relates to the section of the injection device 102 through or on which the selected dosage is visible.

Turning the dosage knob 212 may cause a mechanical click sound to provide acoustical feedback to a user. The numbers displayed in the dosage window 213 are printed on a sleeve that is contained in the housing 203 and mechanically interacts with the drive mechanism 206. When the needle 209 is inserted into a skin portion of the patient, and then an injection button 211 is pushed, the medicament is ejected from the injection device 102. Ejection of the dose may also cause a mechanical click sound. Such a mechanical click sound may be different from the sounds produced when the dosage knob 212 is turned.

The injection device 102 may be used for several injection processes until either the cartridge 204 is empty or the expiration date of the injection device 102 (e.g., 28 days after the first use) is reached. In some examples, before using the injection device 102 for the first time, it may be necessary to perform a "prime shot" to remove air from the cartridge 204 and the needle 209, for example, by selecting two units of medicament and pressing the injection button 311 while holding the injection device 102 with the needle 209 oriented upwards.

The injection device 102 may include one or more components affixed to and/or incorporated in respective components of the injection device 102 that are configured to interact with the add-on device 104. For example, the one or more components may be configured to wirelessly communicate with and/or provide wireless signals to the add-on device 104, and the add-on device 104 may be configured to awaken from a sleep state into an enabled state and/or determine the position of the respective components of the injection device 102 based on characteristics of the wireless signals.

In the example illustrated in FIG. 2, a first Wiegand wire 224 is provided on (e.g., affixed to) the needle shield 220 and a second Wiegand wire 226 is provided on (e.g., affixed to) the drive mechanism 206, in particular, on the piston 208 of the drive mechanism. Each Wiegand wire 224, 226 includes an outer shell and an inner core. A magnetic coercivity of the outer shell is larger (e.g., significantly larger) that a magnetic coercivity of the inner core. As such, the Wiegand wires 224, 226 exhibit a relatively large magnetic hysteresis. When a magnet is brought near the Wiegand wires 224, 226, the high-coercivity outer shell significantly excludes the magnetic field from the low-coercivity inner core until a particular magnetic threshold is reached. Once the magnetic threshold is reached, the entire Wiegand wire 224, 226 rapidly switches magnetization polarity. This phenomenon is sometimes referred to as the Wiegand effect.

When the magnetization polarity of the inner core switches while the magnetization polarity of the outer shell stays the same, a voltage spike (e.g., in some examples, a relatively large voltage spike) can be induced in a nearby coil (e.g., a sensor coil). The magnitude of the induced voltage is proportional to the switchover speed. Because the switchover speed in the Wiegand wire 224, 226 is relatively fast (e.g., a few microseconds) as compared to switchover speeds that would occur in a wire with a relatively smaller magnetic hysteresis, the induced voltage spike can be relatively large and more easily detectable electronically. Once the entire Wiegand wire 224, 226 (e.g., both the inner core and the outer shell) has switched magnetization polarity, the Wiegand wire 224, 226 will retain its polarity until the Wiegand wire 224, 226 is flipped in the opposite direction (e.g., by introducing a magnetic field of the opposite polarity that satisfies a magnetic threshold). When the magnetization polarity of the inner core switches again, a second voltage spike can be induced in a nearby coil. The second voltage spike may have a polarity opposite of a polarity of the first voltage spike.

In the example illustrated in FIG. 2, each of the Wiegand wires 224, 226 is positioned on a movable component of the injection device 102. For each Wiegand wire 224, 226, a sensor coil and magnets of opposite polarity may be positioned in a fixed position relative to the respective Wiegand wire 224, 226 such that movement of the corresponding component of the injection device 102 causes the respective Wiegand wire 224, 226 to transition from a magnetic field of a first polarity to a magnetic field of a second polarity, thereby inducing a voltage spike in the corresponding coil. As such, the position of the corresponding component of the injection device can be inferred based on a time at which the voltage spike occurs, as described in more detail below. In some implementations, the sensor coils and magnets may be incorporated into the add-on device 104.

Figure 3:
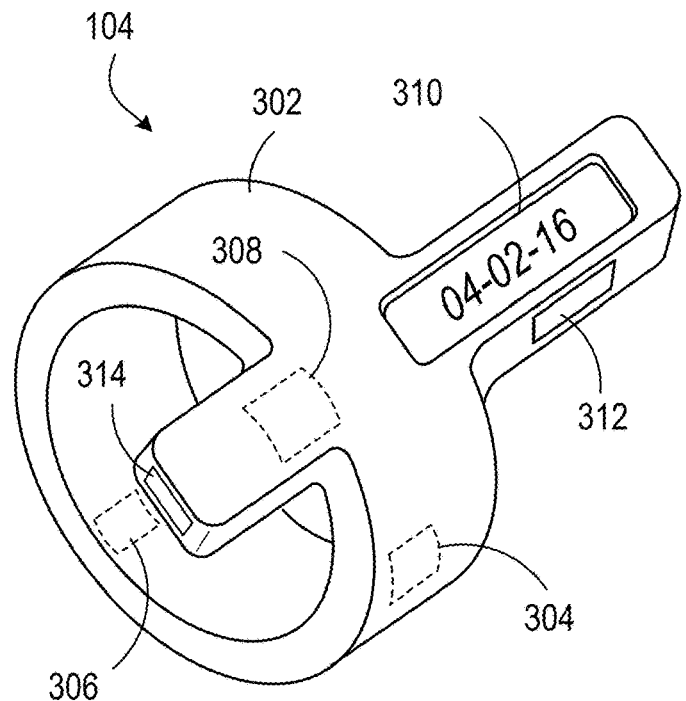
FIG. 3 is an example of the add-on device of FIGS. 1 and 2.

FIG. 3 shows an example of the add-on device 104 of FIGS. 1 and 2. The add-on device 104 includes a housing 302 that is configured to attach (e.g., removably attach) to the injection device 102. In some implementations, the add-on device 104 has a sleeve shape (e.g., cylinder shape) that is configured to slide along a length of the injection device 102 and fix in place around the housing 203 of the injection device 102.

The add-on device 104 includes a first sensor assembly 304, a second sensor assembly 306, and a microcontroller 308 that can include one or more processors and one or more memory devices. In some implementations, the one or more memory devices include one or more non-transitory computer-readable medium storing instructions operable to cause the one or more processors to perform operations. The first sensor assembly 304 is positioned such that the first sensor assembly 304 resides proximate to the first Wiegand wire 224 of the needle shield 220 of the injection device 102 when the add-on device 104 is attached to the injection device, and the second sensor assembly 306 is positioned such that the second sensor assembly 306 resides proximate to the second Wiegand wire 226 of the drive mechanism 206 of the injection device 102 when the add-on device 104 is attached to the injection device, as described in more detail below. The one or more processors of the microcontroller 308 are configured to receive signals from the first sensor assembly 304 and the second sensor assembly 306.

The add-on device 104 optionally includes a display 310 that is configured to present information, such as date/time information and/or instructions for assisting the patient in operating the injection device 102. For example, the display 310 may be configured to present a current date/time, a date/time at which an injection has been administered, instructions to assist the patient in starting, holding, and/or completing an injection, etc.

The add-on device 104 may include a power source such as a battery 312, for example, a coin cell battery. The add-on device may also include a data communication interface 314, such as a Universal Serial Bus (USB) interface, for transferring data from the add-on device 104 to one or more other computing devices. In some implementations, the add-on device may be configured to wireless communication with one or more other computing devices by other means, such as a short-range wireless protocol (e.g., Bluetooth).

Figure 4:
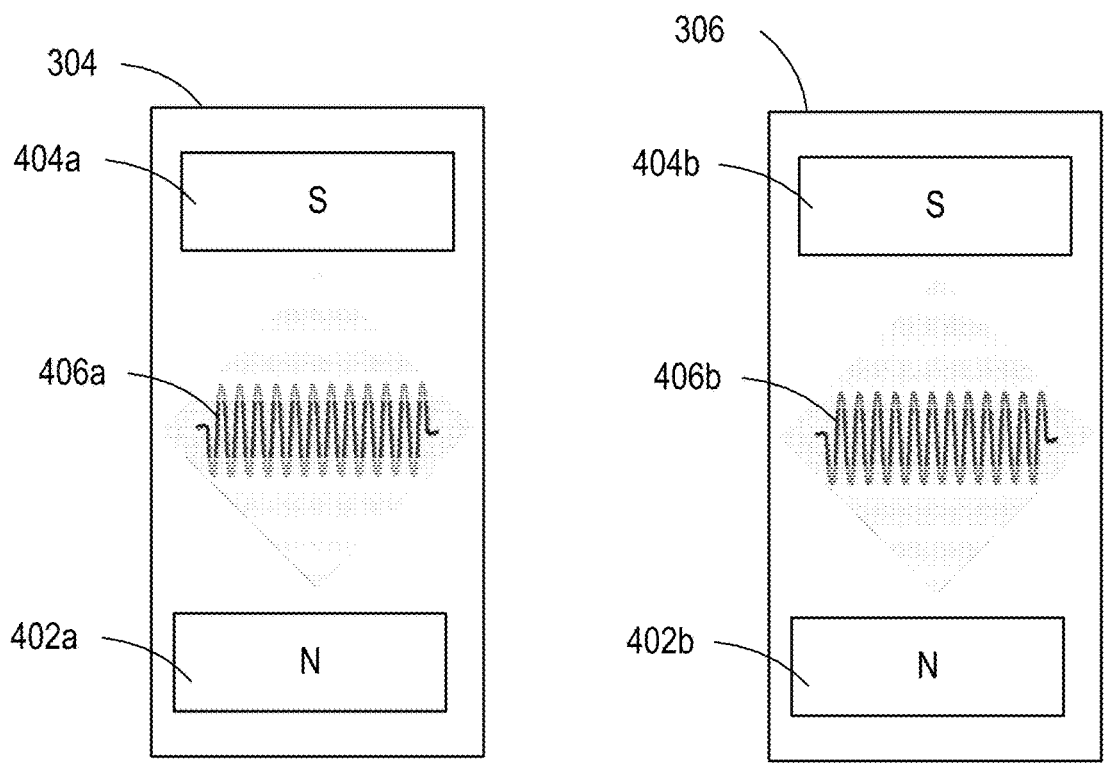
FIG. 4 shows examples of block diagrams of a first sensor assembly and a second sensor assembly of the add-on device.

FIG. 4 shows example of block diagrams of the first sensor assembly 304 and the second sensor assembly 306 of FIG. 3. Each sensor assembly 304, 306 includes a first magnet 402a, 402b having a first polarity and a second magnet 404a, 404b having a second (e.g., opposite) polarity.

In some implementations, the first magnets 402a, 402b have a North polarity and the second magnets 404a, 404b have a South polarity. Each sensor assembly 304, 306 also includes a coil 406a, 406b (e.g., sensor coils). Voltage pulses/spikes can be induced in the coils 406a, 406b in response to a changing magnetic field (e.g., caused by the respective Wiegand wire 324, 326 transitioning from a magnetic field of a first polarity to a magnetic field of a second polarity as the respective Wiegand wire 324, 326 moves from a first position proximate to one of the magnets to a second position proximate to the other magnet).

FIGS. 5A-D show various positions of the first Wiegand wire 224 of FIG. 2 relative to the first sensor assembly 304. A front view of the injection device 102 is shown in the illustrations. For clarity, the illustrations are not drawn to scale in order to focus on the portions of the system 100 relevant to this accompanying description. Further, the illustrations omit the housing 302 and other components of the add-on device 104.

Figure 5A:
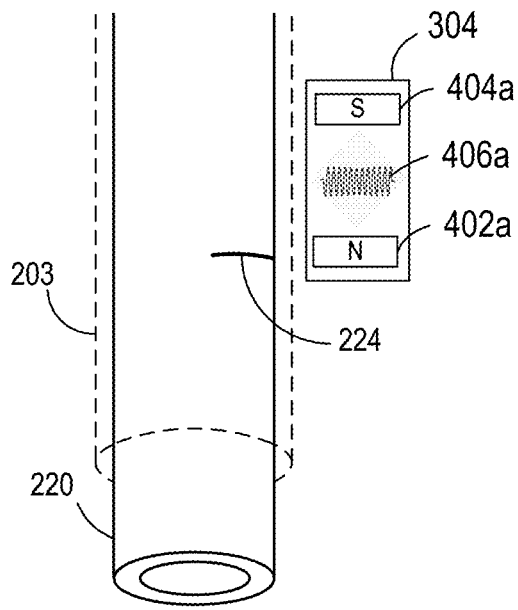
FIGS. 5A-D show various positions of a first Wiegand wire of the injection device relative to the first sensor assembly.

In FIG. 5A, the needle shield 220 is in the extended position. The needle shield 220 may be in the extended position by default (e.g., in the absence of pressure being applied to the needle shield 220) to prevent inadvertent contact with the needle 209. The state of the injection device 102 shown in FIG. 5A may correspond to a time before the injection of the medicament has commenced. When the needle shield 220 is in the extended position, the first Wiegand wire 224 of the needle shield 220 is substantially in line with the first magnet 402a of the first sensor assembly 304. In the illustrated position, the first Wiegand wire 224 is saturated in a magnetic field having the first polarity (e.g., a North polarity). That is, the magnetic field provided by the first magnet 402a when the first Wiegand wire 224 is positioned as illustrated satisfies a magnetic threshold that causes the polarities of the outer shell and the inner core of the first Wiegand wire 224 to orient in the same direction. When the polarities of the outer shell and the inner core remain oriented in the same direction (e.g., when no switching of magnetization polarity occurs in the first Wiegand wire 224), no voltage spike is induced in the coil 406a.

Figure 5B:
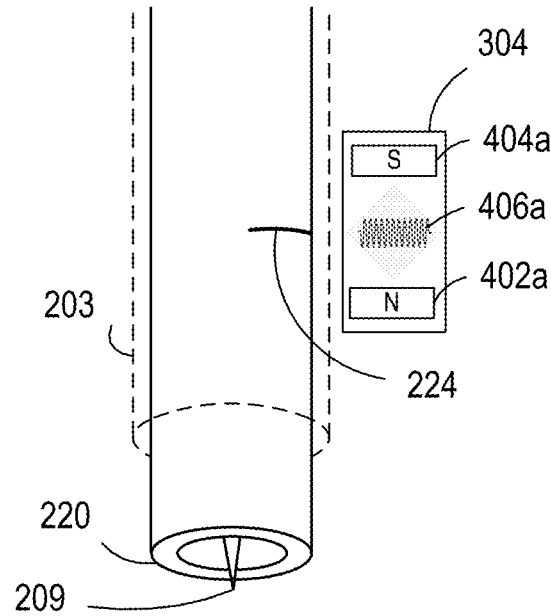

In FIG. 5B, the needle shield 220 begins to move from the extended position to a retracted position. The state of the injection device 102 shown in FIG. 5B may correspond to a time at which the patient begins to press the needle 209 into his or her skin. Such a time may be indicative of a start time of the injection of the medicament. As the needle shield 220 retracts, the first Wiegand wire 224 is introduced to a magnetic field having a second, opposite polarity (e.g., a South polarity) provided by the second magnet 404a. As the needle shield 220 continues to retract and the first Wiegand wire 224 moves closer to the second magnet 404a, the strength of the South polarity magnetic field increases until a magnetic threshold is reached that causes the magnetization polarity of the inner core to switch. Such switching induces a voltage spike in the coil 406a. The coil 406a may provide a signal (e.g., including the voltage spike) to the microcontroller 308 of the add-on device 104. In some implementations, the signal is provided to an analog-to-digital (A/D) converter, and the A/D converter provides a digital signal to the microcontroller 308. A time of receipt of the signal is indicative of the start time of the injection. The time of receipt may be recorded if the voltage spike satisfies a predetermined threshold value.

In some implementations, the add-on device 104 may be in a sleep state before injection commences. For example, the add-on device 104 (e.g., including the microcontroller 308) may be in a state in which the add-on device 104 consumes little or no power. As described above, as the needle shield 220 begins to move from the extended position to the retracted position, the state of the injection device 102 (e.g., as shown in FIG. 5B) may correspond to a time at which the patient begins to press the needle 209 into his or her skin. At such a time, it may be desirable for the add-on device 104 to "wake up" (e.g., enter an enabled state from the sleep state). Upon waking up, electronics of the add-on device 104 can enter a state in which the electronics can process data and/or signals from one or more electrical components.

The voltage spike induced in the coil 406a may cause the add-on device 104 to enter an enabled state. In particular, the coil 406a may provide the voltage spike to the microcontroller 308, which causes the microcontroller 308 to enter an enabled state. In some implementations, the voltage spike may be provided to a switching circuit (e.g., an interval switch circuit), and the switching circuit may cause the microcontroller 308 to enter the enabled state. In some implementations, the voltage spike may be provided to the interval switch via a voltage rectifier. The interval switch circuit may operate in a similar manner as an electronic relay. In some implementations, the interval switch circuit may be a transistor base emitter switch.

The voltage spike may cause the microcontroller 308 (e.g., and the add-on device 104) to enter the enabled state for a predetermined amount of time. For example, the microcontroller 308 may remain in the enabled state for 10-15 seconds to allow the injection to complete and to allow information related to the injection to be stored, as described in more detail below. During the time that the microcontroller 308 is in the enabled state, data processing is supported by the power source (e.g., the battery 312). In some implementations, the microcontroller 308 may remain in the enabled state until a second voltage pulse (e.g., corresponding to the end of the injection) is received at the microcontroller 308, as described in more detail below.

Figure 5C:
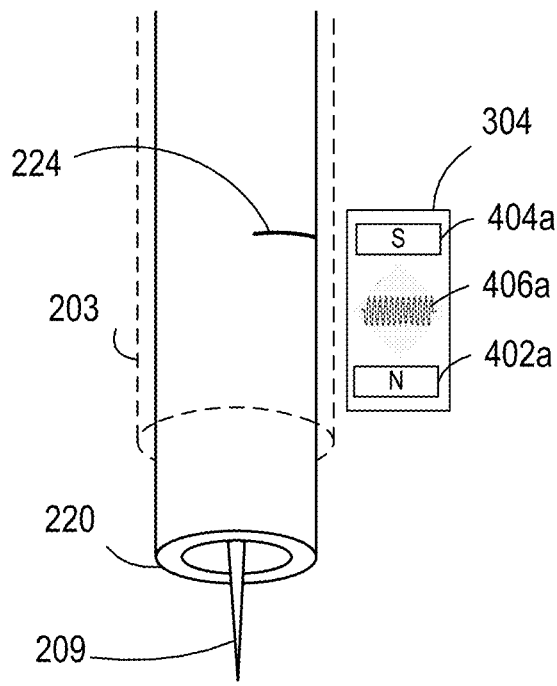

In FIG. 5C, the needle shield 220 continues to move to a further retracted position. The state of the injection device 102 shown in FIG. 5C may correspond to a time during which the patient holds the injection device 102 against his or her skin (e.g., during which the injection is completed). As the needle shield 220 continues to retract, the first Wiegand wire 224 is substantially in line with the second magnet 404a. During the continued retraction, the strength of the South polarity magnetic field increases until a magnetic threshold is reached that causes the magnetization polarity of the outer shell to switch to the same magnetization polarity of the inner core. Such switching induces a voltage spike in the coil 406a. Such a voltage spike may be significantly smaller than the voltage spike that occurs in the arrangement illustrated in FIG. 5B. The coil 406a may provide a signal (e.g., including the voltage spike) to the microcontroller 308 (e.g., via an A/D converter). However, in some implementations, the microcontroller 308 may be configured to ignore the signal if the voltage spike does not have a magnitude that satisfies a predetermined threshold.

Figure 5D:
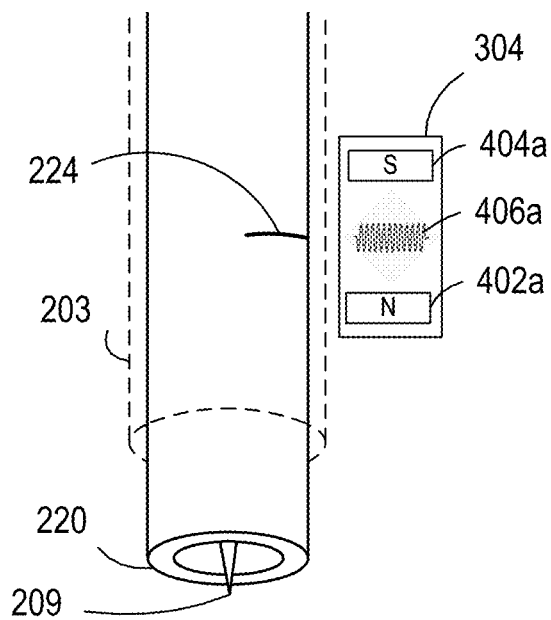

In FIG. 5D, the needle shield 220 begins to move from the retracted position toward the extended position. The state of the injection device 102 shown in FIG. 5D may correspond to a time at which the patient begins to remove the injection device 102 from his or her skin. Such a time may be indicative of a holding time (e.g., an end of a hold). The holding time may represent a dwell time, such as an amount of time the patient should continue to hold the injection device 102 at the injection site (e.g., against the skin) once the injection has completed and the medicament has been injected. Such a holding time can ensure that all medicament has been injected. As the needle shield 220 extends, the first Wiegand wire 224 is reintroduced to the magnetic field having the first polarity (e.g., the North polarity) provided by the first magnet 402*a*. As the needle shield 220 continues to extend and the first Wiegand wire 224 moves closer to the first magnet 402*a*, the strength of the North polarity magnetic field increases until a magnetic threshold is reached that causes the magnetization polarity of the inner core to switch. Such switching induces a voltage spike in the coil 406*a*. The voltage spike may have a similar magnitude and an opposite polarity as the voltage spike that occurs in the arrangement illustrated in FIG. 5B. The coil 406*a* may provide a signal (e.g., including the voltage spike) to the microcontroller 308 (e.g., via an A/D converter). A time of receipt of the signal is indicative of the holding time. The time of receipt may be recorded if the voltage spike satisfies a predetermined threshold value.

FIGS. 6A-C show various positions of the second Wiegand wire 226 of FIG. 2 relative to the second sensor assembly 306. A side view of the injection device 102 is shown in the illustrations. For clarity, the illustrations are not drawn to scale in order to focus on the portions of the system 100 relevant to this accompanying description. Further, the illustrations omit the housing 302 and other components of the add-on device 104.

In FIG. 6A, the drive mechanism 206 is in a substantially retracted position. The state of the injection device 102 shown in FIG. 6A may correspond to a time before an injection is commenced. For example, with the medicament contained in the cartridge 204, the stopper 207 of the drive mechanism 206 may be disposed at the distal end of the cartridge 204. When the drive mechanism 206 is in the retracted position, the second Wiegand wire 226 positioned on the piston 208 is substantially in line with the second magnet 404*b* of the second sensor assembly 306. In the illustrated position, the second Wiegand wire 226 is saturated in a magnetic field having the second polarity (e.g., a South polarity). That is, the magnetic field provided by the second magnet 404*b* when the second Wiegand wire 226 is positioned as illustrated satisfies a magnetic threshold that causes the polarities of the outer shell and the inner core of the second Wiegand wire 226 to orient in the same direction. When the polarities of the outer shell and the inner core remain oriented in the same direction (e.g., when no switching of magnetization polarity occurs in the second Wiegand wire 226), no voltage spike is induced in the coil 406*b*.

In FIG. 6B, the drive mechanism 206 is in a substantially extended position. The state of the injection device 102 shown in FIG. 6B may correspond to a time at which the injection has finished (e.g., an end time of the injection). For example, after the needle 209 of the injection device 102 is inserted into the patient's skin (e.g., corresponding to the position illustrated in FIG. 5C), the patient may press the injection button 211 to cause the piston 208 to push the stopper 207 toward the proximal end of the cartridge 204, thereby causing the medicament to be ejected. When the piston 208 is substantially extended, the second Wiegand wire 226 is introduced to the first magnetic field (e.g., having the North polarity) provided by the first magnet 402*b*. As the piston 208 extends, the strength of the North polarity magnetic field increases until a magnetic threshold is reached that causes the magnetization polarity of the inner core to switch. Such switching induces a voltage spike in the coil 406*b*. The coil 406*b* may provide a signal (e.g., including the voltage spike) to the microcontroller 308 of the add-on device 104 (e.g., via an A/D converter). A time of receipt of the signal is indicative of the end time of the injection. The time of receipt may be recorded if the voltage spike satisfies a predetermined threshold value.

The voltage spike induced in the coil 406*b* may cause the add-on device 104 to enter the sleep state. In particular, the coil 406*b* may provide the voltage spike to the microcontroller 308, which causes the microcontroller 308 to reenter the sleep state from the enabled state. In some implementations, the voltage spike may be provided to the switching circuit, as described above. In some implementations, the microcontroller 308 may remain in the enabled state for a particular length of time (e.g., 5-10 seconds) after receipt of the voltage spike before reentering the sleep state. Such a time delay may allow the injection to complete and allow information related to the injection to be stored.

In FIG. 6C, the drive mechanism 206 returns to the substantially retracted position. The state of the injection device 102 shown in FIG. 6C may correspond to the injection device 102 being prepared for housing another dose of medicament for a subsequent injection. For example, in some implementations, the cartridge 204 may be refilled and the stopper 207 may be returned to the distal end of the cartridge 204 in preparation for another injection. In some implementations, the cartridge 204 may be replaced with a new cartridge, and the stopper 207 may be positioned at a distal end of the new cartridge in preparation for another injection. When the drive mechanism 206 is returned to the retracted position, the second Wiegand wire 226 is substantially in line with the second magnet 404*b* of the second sensor assembly 306. In the illustrated position, the second Wiegand wire 226 becomes resaturated in the South polarity magnetic field, thereby causing the polarities of the outer shell and the inner core of the second Wiegand wire 226 to again orient in the same direction. In this way, the second Wiegand wire 226 is put into a state in which the magnetization polarity of the inner core can again switch when the drive mechanism 206 is extended for a subsequent injection, thereby allowing and end time of a subsequent injection to be recorded.

The system 100 (e.g., the add-on device 104) is configured to determine a status of the injection of the medicament based on the times of receipt of the signals described above with respect to FIGS. 5A-D and 6A-C. For example, the time of receipt of the signal described with respect to FIG. 5B may be identified and/or recorded as the start time of the injection; the time of receipt of the signal described with respect to FIG. 5D may be identified and/or recorded as the hold time of the injection (e.g., the end of the hold); the time of receipt of the signal described with respect to FIG. 6B may be identified and/or recorded as the end of the injection. Additional status information may be determined based on the start, end, and/or hold times, such as the duration of the injection, among others. For example, an elapsed time between the start time and the end time can correspond to the duration of the injection. The status information may be used to record a history of one or more injections provided by the injection device 102. Such status information can be used to ensure that the patient is adhering to a prescribed medication regimen and/or to correlate the health of the patient with the recorded injection times.

In some implementations, some or all of the status information may be stored by the microcontroller 308. For example, the status information may be stored in the one or more memory devices of the microcontroller 308. In some implementations, the one or more memory devices include a non-volatile memory that does not require a continuous supply of power to store data, such as a ferroelectric random access memory (FRAM). In other words, the non-volatile memory may be configured for storing data absent a continuous power supply. Such memory may assist the add-on device 104 in preserving power, thereby facilitating prolonged use. Use of a FRAM in addition to employing a wake-up mechanism on the microcontroller 308, as described above, may provide a low-power solution to the add-on device 104 that requires minimal battery capacity for prolonged use.

In some implementations, some or all of the status information may be provided by the add-on device 104 to a separate device (e.g., a separate computing device). In some implementations, the status information may be transmitted to a connected computing device, such as a smartphone, a laptop, etc. that is connected to the add-on device 104 via the data communication interface (e.g., the USB interface). In some implementations, the add-on device 104 may include a transceiver that is configured to transmit (e.g., wirelessly) the status information to remote computing devices, such as a server (e.g., a cloud server). In some implementations, the status information may be transmitted to a medical server and/or directly to a medical professional. In this way, status information related to injections can be provided to remote medical entities for analysis and/or further treatment recommendations.

Figure 7:
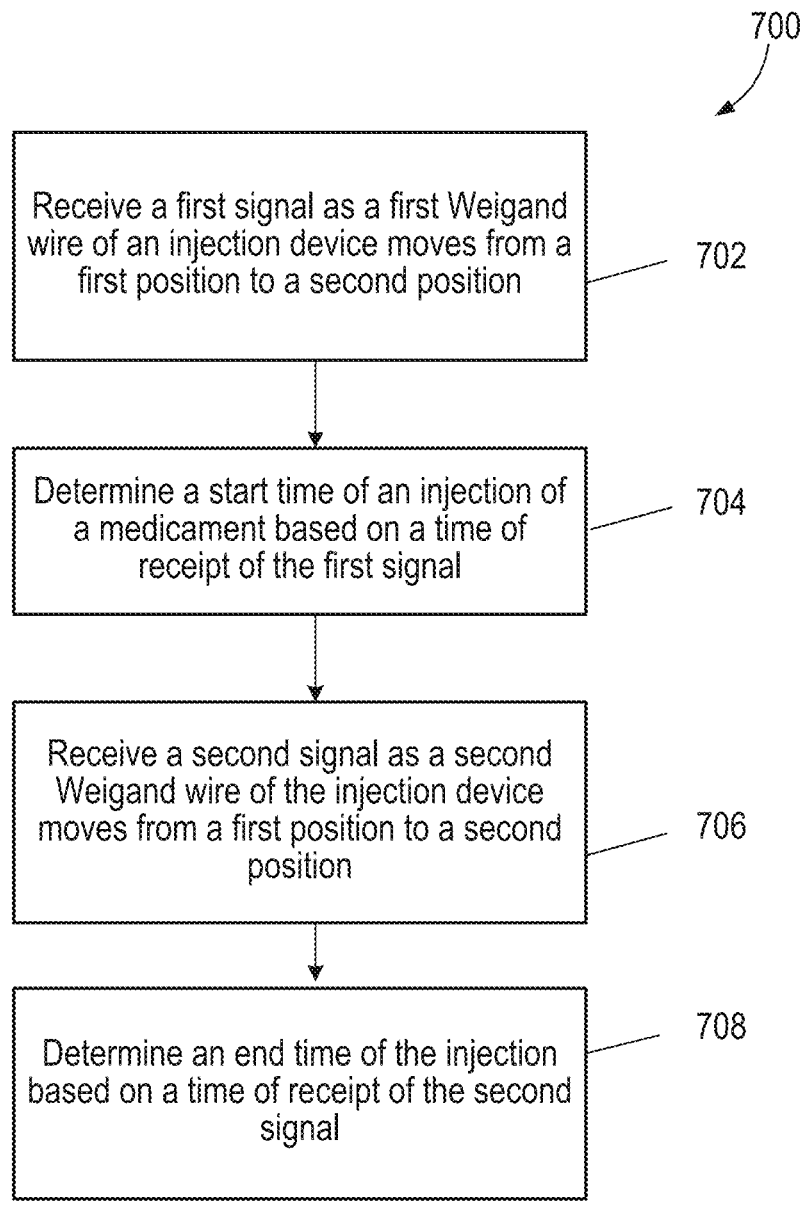
FIG. 7 is a flowchart of an exemplary process of determining the status of the injection of the medicament.

FIG. 7 is a flowchart of an exemplary process 700 of determining a status of an injection of a medicament from an injection device, such as the injection device 102 of FIGS. 1, 2, 5A-D, and 6A-C. The process 700 may be performed by components of an electronic device, such as the add-on device 104 of FIGS. 1, 3, 5A-D, and 6A-C.

At step 702, a first signal is received as a first Wiegand wire 224 of the injection device 102 moves from a first position to a second position. For example, the first signal may be received by the electronic device configured for attachment to the injection device 102. The first signal may be received from the coil 406a of the first sensor assembly 304 as the first Wiegand wire 224 moves from the first position proximate to one magnet (e.g., the first magnet 402a) to the second position proximate to another magnet (e.g., the second magnet 404a) having an opposite polarity as the first magnet 402a. The first Wiegand wire 224 may be affixed to the needle shield 220 of the injection device 102.

At step 704, a start time of the injection of the medicament is determined based on a time of receipt of the first signal. For example, the movement of the first Wiegand wire 224 may correspond to the needle shield 220 of the injection device 102 moving from an extended position to a retracted position. Such a movement of the needle shield 220 may correspond to a time at which the patient begins to press the needle 209 into his or her skin.

At step 706, a second signal is received as a second Wiegand wire 226 of the injection device 102 moves from a first position to a second position. For example, the second signal may be received by the electronic device from the coil 406b of the second sensor assembly 306 as the second Wiegand wire 226 moves from the first position proximate to one magnet (e.g., the second magnet 404b) to the second position proximate to the one magnet and another magnet (e.g., the first magnet 402b) having an opposite polarity as the second magnet 404b. In some implementations, the second position is closer to the first magnet 402b than the second magnet 404b. The second Wiegand wire 226 may be affixed to the drive mechanism 206 of the injection device 102.

At step 708, an end time of the injection is determined based on a time of receipt of the second signal. For example, the movement of the second Wiegand wire 226 may correspond to the drive mechanism 206 of the injection device 102 being in a substantially extended position. Such a movement of the drive mechanism 206 may correspond to a time at which the medicament is fully ejected from the cartridge 204.

In some implementations, a third signal is received as the first Wiegand wire 224 moves from the second position toward the first position. For example, the third signal may be received from the coil 406a of the first sensor assembly 304. A holding time of the injection is determined based on a time of receipt of the third signal.

In some implementations, each of the signals includes a voltage spike of a magnitude that satisfied a predetermined threshold. In some implementations, a sign of the voltage spike in the first signal is opposite of a sign of the voltage spike in the second signal.

While a number of implementations have been described herein, other implementations are possible.

While the sensor assemblies have been described as including two magnets, in some implementations, the magnets may be positioned elsewhere in the system. For example, in some implementations, magnets may be positioned on the injections device and/or at a separate component of the system. The magnets may be positioned relative to the corresponding Wiegand wire such that the Wiegand wire can provide signals (e.g., voltage spikes) to the coil of the corresponding sensor assembly, as described with respect to FIGS. 5A-D and 6A-C. In some implementations, one or more of the magnets may be incorporated into the housing of the injection device. For example, a first magnet may be incorporated into the housing of the injection device at a position near a starting position (e.g., a default position) of one of the Wiegand wires, thereby saturating the Wiegand wire in a magnetic field of a first polarity. A second magnet may be incorporated into the housing of the injection device at a position near a target position of one of the Wiegand wires (e.g., a position that is to correspond to a start time, and end time, and/or a holding time of the injection). In this way, the Wiegand wire can cause a voltage spike to be generated in the corresponding coil when the Wiegand wire reaches the target position.

In some implementations, a Wiegand wire or a magnet may be positioned on the piston such that a time at which the piston starts to move from the distal end of the cartridge toward the proximal end of the cartridge is recorded. Detection of such a movement of the piston can be performed by the sensor assembly described above or by a separate sensor assembly.

While the sensor assemblies have been described as including the magnets and the injection device has been descried as including the Wiegand wires, in some implementations, the magnets may be positioned at the injection device and the Wiegand wires may be positioned at the sensor assemblies (e.g., at the add-on device). For example, one or more magnets may be incorporated into the needle shield and/or the piston, and corresponding Wiegand wires may be positioned next to or within the coil at the respective sensor assembly. Such a configuration may cause relatively larger voltage spikes (e.g., 3.5-5 V) as compared to configurations in which the Wiegand wires are incorporated in the needle shield and the piston (e.g., which may cause voltage spikes of less than 3.5 V).

Configurations that result in relatively smaller voltage spikes (e.g., less than 3.5 V) may be sufficient for implementations in which the voltage spike is largely used to cause the add-on device to "wake up" (e.g., enter the enabled state). For example, implementations in which the Wiegand wires are incorporated into the needle shield and the piston and the magnets are incorporated in the add-on device may be sufficient when the voltage spikes are used to cause the add-on device to enter the enabled state (e.g., and not used to cause information related to the injection to be stored). Such configurations may be desirable for such implementations because incorporating Wiegand wires into the injection device may be easier (e.g., and less costly) than incorporating magnets into the injection device. On the other hand, configurations that result in relatively larger voltage spikes (e.g., 3.5-5 V) may be desirable for implementations in which the voltage spikes are used to cause information related to the injection to be stored because such larger voltage spikes (e.g., larger output signals) can improve the detectability of the corresponding state of the injection device.

While the sensor assemblies or the injection device have been described as including one or more magnets, in some implementations, other magnetic materials may additionally or alternatively be used. For example, in some implementations, rather than magnets being incorporated into the needle shield and/or the piston, a portion of the needle shield and/or the piston may itself be magnetic. In some implementations, the needle shield and/or the piston may include a magnetized plastic material that acts in a manner similar to that described above with respect to the North and South polarity magnets. In this way, a voltage spike can be induced in the corresponding coil as the magnetized plastic material moves proximate the coil.

In some implementations, a variable dose injection device (e.g., a SoloSTAR® Pen made by Sanofi®) can be configured to interact with a sensor assembly similar to the sensor assemblies described above (e.g., the sensor assembly 304). The variable dose injection device may be similar to the injection device 102 described above. For example, the sensor assembly may be used to detect and/or record a selected dose for injection by the variable dose injection device. In some implementations, the sensor assembly may be incorporated into a separate device (e.g., a separate add-on device) that is positioned proximate to a dosage knob of the variable dose injection device. The separate add-on device may be substantially similar to the add-on device 104 described above, with some modifications made to the housing to facilitate attachment to the appropriate portion of the variable dose injection device. For example, the dosage knob may include a plurality of Wiegand wires that are each positioned around a perimeter of the dosage knob. The Wiegand wires may be positioned equidistant from each other such that each Wiegand wire is corresponds to an increment of a dosage indicated on the dosage knob. Each Wiegand wire may be positioned at a location on the dosage knob that "clicks" into place as the dosage knob is rotated. In this way, each click may correspond to an increment of a dosage. In some examples, the dosage knob rotates in single increments of International Units (IU). Thus, for each click as the dosage knob is rotated, a separate Wiegand wire is rotated proximate to the sensor assembly. Each time a Wiegand wire is rotated proximate to the sensor assembly (e.g., as the Wiegand wire moves from a first position proximate to one magnet to a second position proximate to the other magnet), a voltage pulse is generated in the coil. Each voltage pulse can cause a counter of the sensor assembly to increment, such that a value stored by the counter corresponds to the number of IU of the dialed dosage. Such dosage information can be stored along with the start, end, and holding time of the injection.

Figure 8:
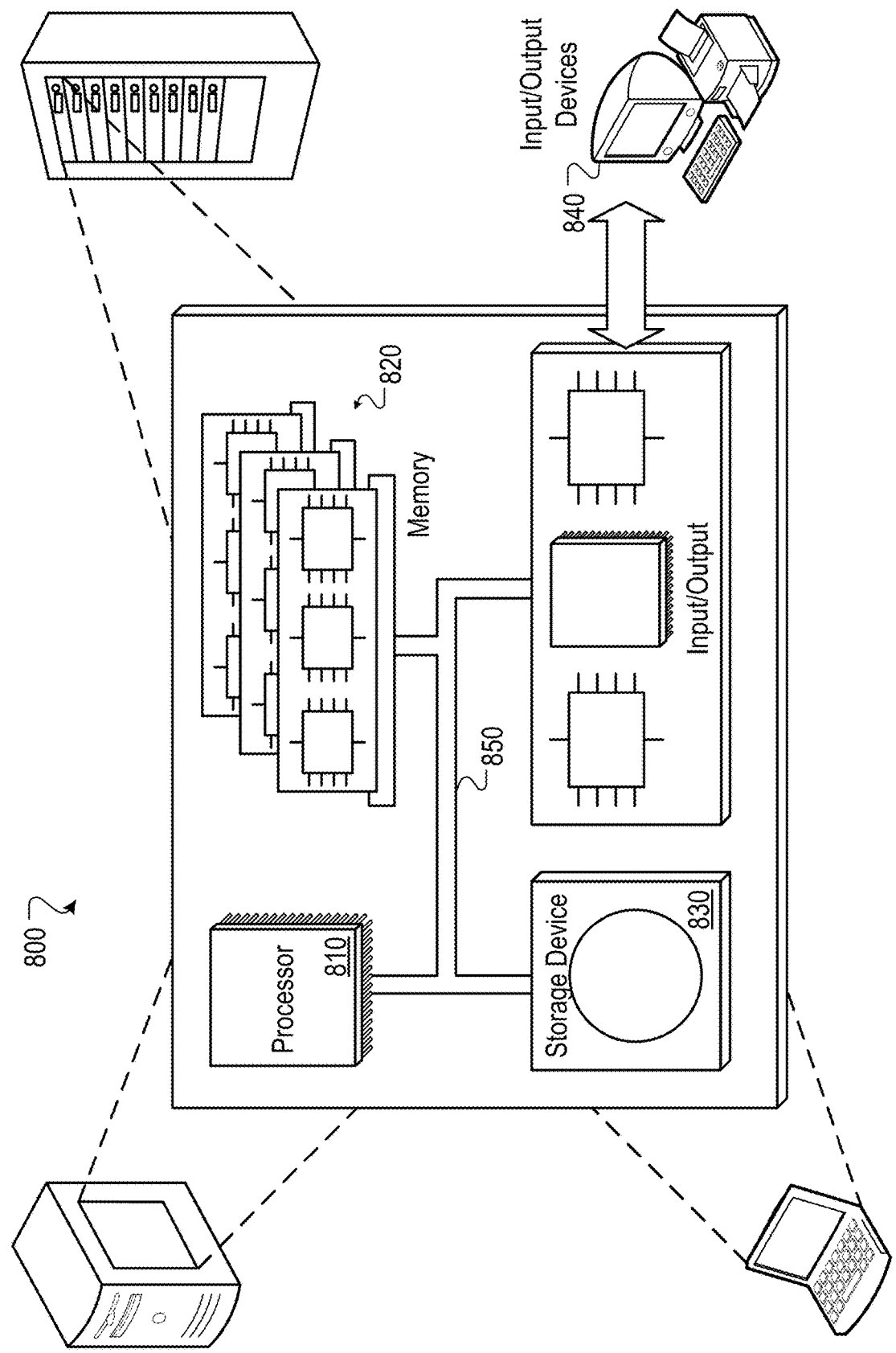
FIG. 8 is a block diagram of an example computer system.

FIG. 8 is a block diagram of an example computer system 800. For example, the add-on device 104 of FIGS. 1 and 3 may be an example of the computer system 800. In some implementations, the computer system 800 may be incorporated into the injection device 102 of FIGS. 1 and 2, and/or the injection device 102 may be configured to interact with a separate computer system 800. The system 800 includes a processor 810, a memory 820, a storage device 830, and an input/output device 840. Each of the components 810, 820, 830, and 840 can be interconnected, for example, using a system bus 850. The processor 810 is capable of processing instructions for execution within the system 800. The processor 810 can be a single-threaded processor, a multi-threaded processor, or a quantum computer. The processor 810 is capable of processing instructions stored in the memory 820 or on the storage device 830. The processor 810 may execute operations to cause the add-on device 104 to determine the status of the injection of the medicament according to the process described above (e.g., the process 700 of FIG. 7).

The memory 820 stores information within the system 800. In some implementations, the memory 820 is a computer-readable medium. The memory 820 can, for example, be a volatile memory unit or a non-volatile memory unit. In some implementations, the memory 820 stores information related to the status of an injection of the medicament, such as time data indicating a start time of an injection, and end time of an injection, a holding time of an injection, a duration of an injection, etc.

The storage device 830 is capable of providing mass storage for the system 800. In some implementations, the storage device 830 is a non-transitory computer-readable medium. The storage device 830 can include, for example, a hard disk device, an optical disk device, a solid-date drive, a flash drive, magnetic tape, or some other large capacity storage device. The storage device 830 may alternatively be a cloud storage device, e.g., a logical storage device including multiple physical storage devices distributed on a network and accessed using a network. In some implementations, the information stored on the memory 820 can also or instead be stored on the storage device 830.

The input/output device 840 provides input/output operations for the system 800. In some implementations, the input/output device 840 includes one or more of network interface devices (e.g., an Ethernet card), a serial communication device (e.g., an RS-232 port), and/or a wireless interface device (e.g., a short-range wireless communication device, an 802.11 card, a 3G wireless modem, or a 4G wireless modem). In some implementations, the input/output device 840 includes driver devices configured to receive input data and send output data to other input/output devices, e.g., a keyboard, a printer, and display devices. In some implementations, mobile computing devices, mobile communication devices, and other devices are used.

In some implementations, the system 800 is a microcontroller. A microcontroller is a device that contains multiple elements of a computer system in a single electronics package. For example, the single electronics package could contain the processor 810, the memory 820, the storage device 830, and input/output devices 840.

Although an example processing system has been described in FIG. 8, implementations of the subject matter and the functional operations described above can be implemented in other types of digital electronic circuitry, or in computer software, firmware, or hardware, including the structures disclosed in this specification and their structural equivalents, or in combinations of one or more of them.

Implementations of the subject matter described in this specification can be implemented as one or more computer program products, e.g., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance that is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some implementations, the antibody has effector function and can fix complement. In some implementations, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full-length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (such as, for example, adjustments, additions, or removals) of various components of the substances, formulations, apparatuses, methods, systems, devices, and implementations described herein may be made without departing from the full scope and spirit of the present inventive concepts, which encompass such modifications and any equivalents thereof.

A number of implementations of the systems and techniques described herein have been presented. Nevertheless, it will be understood that various modifications may be made without departing from the spirit and scope of such system and techniques. Accordingly, other implementations are within the scope of the following claims.

The invention claimed is:
1. An electronic device comprising:
   a housing configured to be attached to an injection device, the housing comprising at least one cylindrical surface configured to be positioned around a housing of the injection device;
   a first coil disposed in the housing of the electronic device and configured to, when the electronic device is attached to the injection device, produce a first voltage pulse indicative of a first status of the injection device as a first Wiegand wire of the injection device moves from a first position proximate to a first magnet to a second position proximate to a second magnet; and
   one or more processors configured to receive the first voltage pulse and determine the first status of the injection device based on a time of receipt of the first voltage pulse.
2. The electronic device of claim 1, further comprising:
   a second coil disposed in the housing of the electronic device and configured to, when the electronic device is attached to the injection device, provide a second voltage pulse indicative of a second status of the injection device as a second Wiegand wire of the injection device moves from a first position proximate to a third magnet to a second position proximate to a fourth magnet,
   wherein the one or more processors are configured to receive the second voltage pulse and determine the second status of the injection device based on a time of receipt of the second voltage pulse.

3. The electronic device of claim 2, wherein the time of receipt of the first voltage pulse is indicative of a start time of an injection of medicament of the injection device and the time of receipt of the second voltage pulse is indicative of an end time of the injection of the medicament.

4. The electronic device of claim 1, wherein at least one of the first magnet and the second magnet is disposed within the housing of the injection device.

5. The electronic device of claim 1, wherein at least one of the first magnet and the second magnet is disposed within the housing of the electronic device.

6. The electronic device of claim 1, wherein the one or more processors are configured to determine a position of a movable component of the injection device based on the received first voltage pulse.

7. The electronic device of claim 1, wherein the housing of the electronic device is configured such that at least one of the first magnet, the second magnet, and the first coil is positioned proximate to the first Wiegand wire of the injection device when the electronic device is attached to the injection device.

8. The electronic device of claim 1, wherein the housing of the electronic device is configured to slide relative to the housing of the injection device to position the electronic device proximate to the first Wiegand wire of the injection device.

9. The electronic device of claim 1, wherein the first magnet has a first polarity and the second magnet has an opposite second polarity.

10. The electronic device of claim 1, wherein the one or more processors are configured to determine whether the received first voltage pulse exceeds a predetermined voltage threshold, and in response to determining that the received first voltage pulse exceeds the predetermined voltage threshold, record a time when the first voltage pulse is received by the one or more processors in a non-volatile memory of the electronic device.

11. The electronic device of claim 1, wherein the one or more processors are configured to change the electronic device between a sleep state and an enabled state based on the received first voltage pulse.

12. An injection device comprising:
a housing;
a medicament container containing a medicament;
a first movable component slidably disposed within the housing and comprising a first Wiegand wire configured to cause a first voltage signal to be produced such that a movement of the first movable component relative to the housing causes the first voltage signal to be produced to indicate a first status of the injection device; and
a second movable component slidably disposed within the housing and comprising a second Wiegand wire configured to cause a second voltage signal to be produced such that a movement of the second movable component relative to the housing causes the second voltage signal to be produced to indicate a second status of the injection device.

13. The injection device of claim 12, wherein the first voltage signal is indicative of a start time of an injection of the medicament of the injection device and the second voltage signal is indicative of an end time of the injection of the medicament.

14. The injection device of claim 12, wherein the first movable component is a needle shield or a dosage knob, and the second movable component is a plunger.

15. The injection device of claim 12, wherein the first movable component is a needle sleeve configured to move between an extended position in which a proximal end of the needle sleeve extends beyond an proximal end of the housing of the injection device and a retracted position in which the needle sleeve is retracted into the housing of the injection device such that movement of the needle sleeve from the extended position to the retracted position causes the first voltage signal to be produced to indicate a start time of an injection of the medicament by the injection device.

16. The injection device of claim 12, wherein the second movable component is a plunger configured to engage a stopper within the medicament container such that movement of the plunger causes the second voltage signal to be produced to indicate an end time of an injection of the medicament by the injection device.

17. The injection device of claim 12, further comprising a third movable component rotatably disposed relative to the housing and comprising a third Wiegand wire such that a movement of the third movable component relative to the housing causes a third voltage signal to be produced to indicate a dose size of a selected medicament for an injection by the injection device.

18. The injection device of claim 17, wherein the third movable component is a dosage knob and the Wiegand wire is disposed on a perimeter of the dosage knob.

19. An electronic device comprising:
a housing configured to be attached to an injection device;
a first coil disposed in the housing and configured to, when the electronic device is attached to the injection device, produce a first voltage pulse indicative of a first status of the injection device as a first Wiegand wire of the injection device moves from a first position proximate to a first magnet to a second position proximate to a second magnet; and
one or more processors configured to receive the first voltage pulse and determine the first status of the injection device based on a time of receipt of the first voltage pulse,
wherein the housing of the electronic device is configured to slide relative to a housing of the injection device to position the electronic device proximate to the first Wiegand wire of the injection device.

20. The electronic device of claim 19, further comprising:
a second coil disposed in the housing of the electronic device and configured to, when the electronic device is attached to the injection device, provide a second voltage pulse indicative of a second status of the injection device as a second Wiegand wire of the injection device moves from a first position proximate to a third magnet to a second position proximate to a fourth magnet,
wherein the one or more processors are configured to receive the second voltage pulse and determine the second status of the injection device based on a time of receipt of the second voltage pulse.

* * * * *